(12) United States Patent
Bonde

(10) Patent No.: US 10,450,386 B2
(45) Date of Patent: *Oct. 22, 2019

(54) METHOD FOR PROCESSING A BIOMASS CONTAINING LIGNOCELLULOSE

(71) Applicant: Kinetic Biofuel A/S, Bælum (DK)

(72) Inventor: Torben Andreas Bonde, Ega (DK)

(73) Assignee: Kinetic Biofuel A/S, Baelum (DK)

( * ) Notice: Subject to any disclaimer, the term of this patent is extended or adjusted under 35 U.S.C. 154(b) by 221 days.

This patent is subject to a terminal disclaimer.

(21) Appl. No.: 15/636,944

(22) Filed: Jun. 29, 2017

(65) Prior Publication Data

US 2017/0298150 A1    Oct. 19, 2017

Related U.S. Application Data

(63) Continuation of application No. 14/391,993, filed as application No. PCT/DK2013/050097 on Apr. 10, 2013, now Pat. No. 9,714,299.

(30) Foreign Application Priority Data

Apr. 11, 2012    (DK) .................................. 2012 70180

(51) Int. Cl.
| | | |
|---|---|---|
| C08B 1/00 | (2006.01) | |
| C12P 7/10 | (2006.01) | |
| D21C 1/02 | (2006.01) | |
| C12P 19/02 | (2006.01) | |
| C12P 19/14 | (2006.01) | |
| C12P 5/02 | (2006.01) | |
| A23K 10/12 | (2016.01) | |
| A23K 10/32 | (2016.01) | |

(52) U.S. Cl.
CPC ................ *C08B 1/00* (2013.01); *A23K 10/12* (2016.05); *A23K 10/32* (2016.05); *C12P 5/023* (2013.01); *C12P 7/10* (2013.01); *C12P 19/02* (2013.01); *C12P 19/14* (2013.01); *D21C 1/02* (2013.01); *C12P 2201/00* (2013.01); *C12P 2203/00* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| | | |
|---|---|---|
| 2004/0185542 A1 | 9/2004 | Yang et al. |
| 2009/0050134 A1 | 2/2009 | Friend et al. |
| 2010/0285556 A1 | 11/2010 | Feldmann |
| 2011/0124057 A1 | 5/2011 | Genta et al. |

FOREIGN PATENT DOCUMENTS

| | | |
|---|---|---|
| CN | 101993752 | 3/2011 |
| CN | 102059075 | 5/2011 |
| CN | 102059076 | 5/2011 |
| JP | 2008274112 A | 11/2008 |
| WO | WO-03/071025 | 8/2003 |
| WO | WO-2006/032282 | 3/2006 |
| WO | 2009011906 A1 | 1/2009 |
| WO | WO-2009045651 | 4/2009 |

OTHER PUBLICATIONS

Machine translation for JP 2007-119272, 9 pgs. (Year: 2007).*
Danish Novelty Search Report in PA 2012 70180, dated Nov. 28, 2012, 2 pages.
PCT International Preliminary Report on Patentability in PCT/DK2013/050097, dated Oct. 7, 2014, 41 pages.
PCT International Search Report in PCT/DK2013/050097, dated Jun. 17, 2013, 3 pages.
PCT International Written Opinion in PCT/DK2013/050097, dated Apr. 23, 2014, 9 pages.

* cited by examiner

*Primary Examiner* — Thane Underdahl
(74) *Attorney, Agent, or Firm* — Servilla Whitney LLC

(57) ABSTRACT

There is disclosed a method for processing a biomass (for example straw) containing lignocellulose such that cellulose and hemicellulose are made accessible for further processing, typically by decomposition, without needing energy-consuming dissolution of the biomass in water.

The method includes repeated compressions of the biomass in a reciprocating piston press, where loose biomass is continuously fed into a piston chamber in front of a piston which moves the loose biomass into a tubular reaction chamber in which the biomass is compressed for producing a vapour explosion and autohydrolysis under simultaneous displacement of compressed biomass through the reaction chamber.

After compression, the biomass can be added fluid livestock manure, fluid waste water sludge etc. in a biogas plant for a subsequent biogas process.

10 Claims, 9 Drawing Sheets

METHOD FOR PROCESSING A BIOMASS CONTAINING LIGNOCELLULOSE

CROSS REFERENCE TO RELATED APPLICATIONS

This is a continuation application of copending U.S. patent application Ser. No. 14/391,993, filed Oct. 10, 2014, which is the National Stage entry of International Application No. PCT/DK2013/050097, filed Apr. 10, 2013, which claims priority to Danish Patent Application No. PA 2012 70180, filed Apr. 11, 2012, the disclosures of which are incorporated herein by reference in their entireties.

FIELD OF THE INVENTION

The present invention concerns a method for processing a biomass (for example straw) containing lignocellulose such that cellulose and hemicellulose are made accessible for further processing, typically by decomposition, which preferably is an enzymatic decomposition. More specifically, the invention concerns a method wherein processed lignocellulose is used for producing biofuels such as for example ethanol, butanol, hydrogen, methanol and biogas.

The invention has appeared in connection with treatment of straw. At several points the invention is therefore explained with reference to straw, but by these explanations it is understood that corresponding advantages are achieved by other kinds of biomass that contain lignocellulose.

BACKGROUND OF THE INVENTION

First generation bioethanol is mainly produced on the basis of cereal crops like wheat and maize as well as sugar cane. This is due to the fact that corn and sugar cane contain readily accessible carbohydrates such as starch that can be converted into sugar in a simple way, and which is subsequently is fermented into ethanol.

However, this production has been critisised for converting good foodstuffs into energy apart from not being sustainable. For some years, research has therefore been made into utilising crop residue from food production for production of biofuel, in particular bioethanol. Research has particularly concentrated on converting straw and wood chips into bioethanol. This type of ethanol is labelled second generation bioethanol or cellulosic ethanol.

Biomass, such as wheat straw and straw from other corn and maize crops and wood, consists largely of cellulose, hemicellulose and lignin why it is also collectively called lignocellulose.

Cellulose is a linear homogenous polymer of up to 15,000 glucose units interconnected by β-1,4-glucoside bonds. Hemicellulose is, however, a heterogeneous branched polymer with a length up to 200 units which can consist of e.g. arabinose, xylose, galactose, mannose and glucose.

Lignin constitutes a network formed by polymerisation of the monomers p-coumaryl alcohol, coniferyl alcohol and sinapyl alcohol. The complex network of lignin encapsulates and contributes to binding cellulose and hemicellulose together. The structure of the plant cell wall is hereby strengthened and protected against decomposition in the nature e.g. by attacks from fungi or insects. In general, lignocellulose contains about 35-50% cellulose, 20-30% hemicellulose and 15-30% lignin.

However, there are great differences in the contents of various plants and the composition of hemicellulose and lignin is very dependent on the species. In general, wood contains more lignin and less hemicellulose than straw, and where hemicellulose in straw mainly consists of arabinose and xylose, in conifers it contains mostly mannose and only a little xylose.

Utilisation of lignocellulose as substrate for various fermentation processes presupposes a prior decomposition of cellulose and hemicellulose into their respective monomers. The first step in this process is a thermochemical treatment of the lignocellulose whereby lignin is released and hemicellulose and cellulose are partially dissolved or made more accessible to enzymes.

The enzymes for decomposing lignocellulose can be divided into two main groups: cellulases and hemicellulases. The last step in the decomposition of cellulose is the cleavage of cellobiosis into two glucose molecules by the enzyme β-glucosidase. The more heterogeneous structure of hemicelluloses means that a greater number of different enzymes are required to completely decompose it into sugar molecules. An example of such a complex enzyme mixture is Novozyme's Cellic. CTec3 which contains different cellulases and hemicellulases as well as other hydrolytic enzymes.

As mentioned, the first step in the utilisation of lignocellulose is a pre-treatment and typically a thermochemical pre-treatment. Steam explosion is one of a wide range of such different thermochemical pre-treatment methods. This process is combined with addition of water and catalysts such as acids and bases or gases like oxygen and sulphur dioxide.

Pre-treatment of biomasses like straw and wood chips for making fluid bio-fuels, especially ethanol, has been subject to a very comprehensive research effort, and a massive amount of scientific literature is thus available on this area.

In the recent years dominating biochemical methods have been described. A comprehensive presentation of these works is not to be made here, but it is, however, to be noted that several groups point to autohydrolysis as the preferred technology because it is not based on chemicals, because formation of inhibitors is modest and because biomass with relatively high dry matter content can be processed. It is also preferred by most authors over wet oxidation in which oxygen is added to the process.

Autohydrolysis is termed differently but is often called thermal hydrolysis, steaming or steam explosion regardless that the explosion part is not necessarily an advantage to the hydrolysis or comminution of the material. The method borders to "liquid hot water treatment", depending on the amount of water, and wet oxidation if oxygen forms part of the process.

The scientific literature furthermore points to the use of a number of chemicals and catalysts or to hydrolysis of lignocellulose, including weak and strong acids and bases and a number of gases like $SO_2$, $CO_2$, $O_2$, $NH_3$, $H_2O_2$, $O_3$. To this is added application of enzymes, either made industrially or as a biological pre-treatment.

The technical installations used for such thermochemical pretreatments of lignocellulose-containing biomasses have only been made in a few examples.

The best known apparatus is the staketech hydrolysator of SunOpta which is used in the first commercial plant for producing bioethanol based on straw. This machine has a horizontal reaction chamber with a screw conveyor moving the straw forward under high pressure and temperature, allowing it to explode into an associated expansion container at frequent intervals, i.e. at intervals of a few seconds. The operating temperature and pressure are 190-210° C. and 15-20 bars, respectively.

The Atlas Stord hydrolysator for hydrolysis of feathers uses a different principle, so-called plug flow, where the reaction chamber is a vertical chamber with a valve at the bottom which opens and closes at intervals of a few seconds. The overpressure in the reaction chamber will thus make the hydrolysed feathers to explode into an expansion container. The reaction chamber is therefore not provided with a shaft passage. The operating temperature and pressure are 160-210° C. and 6-10 bars, respectively.

Finally, Villavicencio (1987) has published an invention for thermochemical treatment of fibres by means of several reaction chambers. The biomass is supplied via screw conveyors, which also act as back pressure valves, to the first reaction chamber.

Common to all techniques are that
1) heat is supplied from an external heat source, particularly by means of hot water or steam;
2) water in the form of liquid water or steam is added to the process such that the dry matter content is at most 30-40% in the reaction chamber, and typically 10%;
3) water or steam is added as a necessary prerequisite for treatment at high temperatures at the level of 160-220° C.

The operational mode of the technique, and as the name "steam explosion" indicates, is a mechanical decomposition of the fibres of the biomass by a steam explosion caused by a sudden pressure drop from e.g. 20 bars to atmospheric pressure. The state of water at e.g. 200° C. under pressure is as a liquid, but when the pressure abruptly drops to atmospheric pressure, part of the water is transformed into steam, meaning the water occurring in all parts of the plant fibres as well. When this water explodes in the cellulose fibres, the biomass is torn up mechanically. This tearing up contributes to make the component parts of lignocellulose of cellulose and hemicellulose accessible for further processing, as for example by enzymatic decomposition.

Conventional steam explosion is often accomplished at temperatures in the range 160-220° C. and corresponding pressures at 0.60-4.83 MPa. The processing time varies from a few seconds to several minutes before the material is exposed to atmospheric pressure via explosive decompression. The process causes decomposition of hemicellulose and transformation of lignin due to the high temperature. Hemicellulose is decomposed by acetic acid and other organic acids formed during the treatment, i.e. via so-called autohydrolysis. Lignin is not decomposed to the same degree but is redistributed on the fibre surfaces as a result of melting and depolymerisation/repolymerisation reactions.

Besides these chemical effects, steam explosion also has a purely mechanical or physical effect as the material explodes and fragments whereby the accessible surface is increased.

The procedure is implemented, as mentioned, by adding water to the biomass, either in the form of liquid water or in the form of steam, or a combination thereof, and heating the mixture. High temperatures are attained by heating with hot water or steam.

The highest dry matter concentration achieved by these systems is about 30-40%, typically much lower, requiring large technical installations due to the amount of water and the voluminous structure of the biomass. Even a compressed straw bale has a density of about 150 kg/m$^3$ which is not much.

A crucial challenge to the technique is the large amounts of water and energy used for pre-treatment and the necessarily large installations for pressure containers, valves, pipes, screw conveyors etc.

This also entails substantial drawbacks by biogas plants since the large addition of water with the straw strains the hydraulic capacity of a biogas plant, and since the energy consumption reduces the net energy production and the cost efficiency.

A biofuel can also be provided in the form of biogas. Until now biomass, preferably in the form of straw, has not been used for biogas production. It is not known to use straw for biogas purposes. It is only known that straw forms part of biogas plants to the extent that straw is used as bedding in livestock production and to the extent that the resulting livestock manure is degassed.

Actually, it is rather surprising that straw is not used for biogas purposes. In the light of the fact that livestock manure, i.e. essentially cattle and pig liquid manure, is fluid with a dry matter content between 4 and 8%, there is room for additional dry matter in the biogas plant, in particular straw.

Straw is a difficult material to handle. It is very abrasive, very hydrophobic and has a very low density, i.e. less than 100 kg per m$^3$. The handling of straw in any connection and in particular in biogas plants therefore requires a special technique.

In addition, straw predominantly consists of cellulosic fibres which are crystalline polymers of (1-4)-β-D-glucose. Hemicellulose forms part thereof which correspondingly is an amorphous and partly crystalline polymer consisting of (1-4)-β-xylose. Hemicellulose forms part of both fibres and cell walls. Lignin, a third essential component of straw, is a polymer of phenol. Hemicellulose as well as lignin protect the cellulose against "weather and wind", and in this connection against decomposition by enzymes and microorganisms.

In order to efficiently utilise straw in a biogas plant it is thus necessary to pretreat the straw in order to open up the fibres of the straw and to make the component parts of the lignocellulose accessible to decomposition. As mentioned above, this will be energy-consuming and necessitate use of voluminous plants.

OBJECT OF THE INVENTION

The object of the present invention is to indicate a method for processing a biomass (for example straw) containing lignocellulose such that cellulose and hemicellulose are made accessible for enzymatic decomposition, in particular with the intention of making biofuels such as for example ethanol and biogas.

DESCRIPTION OF THE INVENTION

According to the present invention, this is achieved by a method which is peculiar by including steps for:
repeated compressions of the biomass in a reciprocating piston press, where loose biomass is continuously fed into a piston chamber in front of a piston which moves the loose biomass into a tubular reaction chamber in which the biomass is compressed for producing a mechanically induced water vapour explosion and autohydrolysis under simultaneous displacement of compressed biomass through the reaction chamber.

By the present invention is thus achieved an efficient method for establishing a first step in the process of utilising lignocellulose as substrate for various processes as the explosion of the water by the mechanically induced steam explosion causes the cellulose fibres to be torn up mechanically. This tearing up make lignocellulose components of cellulose and hemicellulose accessible to subsequent enzymatic decomposition to their respective monomers.

A continuous feeding of the biomass and a simultaneous displacing of compressed biomass through and out of the reaction chamber enable a continuous process in a plant in which there is only need for a processing unit with a very restricted volume. A piston press with capacity of processing 1 ton of biomass per hour can thus have a size less than 3 cubic metres. A further development for larger machines may further optimise this ratio.

The piston stroke acts on the biomass with a pressure between 500 and 3000 bars, in particular between 1000 and 2500 bars. The biomass is hereby compressed to 500-1000 kg/m$^3$ and is directly impacted mechanically. At the same time, the kinetic energy of the piston is deposited in the straw in the form of heat.

The heat formation in the biomass primarily occurs because of friction between the biomass and the walls of the reaction chamber and internal friction in the biomass. The heat formation causes a strong heating of the walls of the reaction chamber and a lesser heating of the biomass. The walls are typically heated to between 110 and 200° C., the biomass to between 60 and 170° C., though locally the temperature rises above 200° C. The compression in the reaction chamber causes the occurrence of very many local steam explosions.

As this water is under pressure, it remains in liquid state until the piston is retracted before a new piston stroke. At retraction, the water explodes and the biomass is impacted as by a steam explosion. This is repeated a number of times until compressed biomass is advanced so far in the compression chamber that piston strokes do no longer influence this biomass.

The action of heat and the steam explosion cause a certain autohydrolysis of the biomass, meaning that steam at high temperature partly dissolves the lignocellulose by a hydrolytic process. By the autohydrolysis there are generated organic acids which lower pH to 4-6, typically pH 5.

The process is distinguished by being very energy economic as there is no need for heating large amounts of water.

Summarising, it can be said that steam explosion is a technique with several cooperating effects: effect of high temperature (i.e. formation of organic acids, lignin melts); effect of autohydrolysis (hemicellulose and partly lignin are decomposed via activity of i.a. acetic acid); and effect of mechanical tearing up.

A mechanical press is designed as an eccentric press. Mechanical presses include a constantly rotating drive mechanism converting a rotating movement into a reciprocating movement of a piston by means of an eccentric. The piston has two extreme positions. At one position the press face of the piston is located in a piston chamber, also called precompression chamber, with the material to be pre-treated, in particular by compression into a briquette, and at the other extreme position the press face of the piston is located at the inlet to an open conical nozzle at the side of the precompression chamber. On its way from one extreme position to the other, the piston pushes some of the material from the chamber in front of itself into the nozzle. The material portions compressed and pre-treated by each stroke of the piston, or in concrete situations formed bio-briquettes, are continuously pushed out through the outlet of the nozzle. Mechanical presses operate at far higher pressures than hydraulic presses as a pressure of at least 800 bar is attained. In a bio-briquette made in a hydraulic press the bonding of the biological material is primarily mechanical and secondarily by adhesion, whereas the bonding of the biological material in a bio-briquette made in a mechanical press is primarily by adhesion and secondarily mechanical. The present invention is used within the technical area of mechanical briquette pressing machines as it concerns high capacity production of bio-briquettes or pre-treatment of biological material.

Reciprocating mechanical briquette-pressing machines for making briquettes, mainly briquettes of wood or other usable biological materials such as fabric, MDF dust, plant fibres, straw, hemp, bark, paper, cardboard, coal dust, domestic waste, livestock manure or sludge, are known. The briquettes can primarily be used for firing in solid fuel furnaces for e.g. domestic space heating. The material is typically a residual product from the wood industry in the form of sawdust or shavings.

The material is to have a moisture content of 5% to 20%, typically 6% to 16%. We are here speaking of percentage by weight. The material is compressed in the die under great pressure and consequent high temperature. The biological material contains cells that among others include water, cellulose and lignin. The purpose of the compressions is to activate the lignin which after cooling provides for binding the material (the bio-briquette) together. During application as pre-treatment and possible addition of organic acid, this is the base for extracting lignin and thereby exposing cellulose and hemicellulose fibres to further processing. The rising pressure in the biological material produces a rise in temperature in the cells, causing the water in the cell to be transformed into steam by a steam explosion whereby the cell wall is destroyed and the lignin is released. The steam explosions are initiated at a pressure of about 400-500 bar and continue while the pressure rises to the maximum value of more than 2000 bar. If the moisture drops below 6%, there is normally not enough moisture in the material for producing enough steam explosions so that a bonding can take place. If the moisture rises over 16%, the steam explosions usually become so strong that the process fragments the briquettes, and the latter are flung out of the machine or back into the system. This can be advantageous as pre-treatment as pre-treatment as such is desired rather than formation of an actual briquette.

As it appears from the above, a more complete decomposition of the cells under formation of the briquette in a mechanical briquette press is achieved due to the higher pressure. The amount of lignin released for subsequent bonding of the bio-briquette is substantially higher.

The biological material leaves the briquette press as a continuous rod. Each piston stroke adds, so to say, a "disc" of biomass to the run of material, and surfaces of fracture are formed between each disc. Mechanical presses are typically used in larger installations from about 200 kg/hour and up to about 2500 kg/hour. In a mechanical press the desired back pressure can therefore only be adjusted by mounting a nozzle with a different conicity or with a variable squeeze nozzle. Due to the fact that the mechanical press is driven by electric motors and not by a hydraulic motor there is only a small energy loss in the machine, and the ratio between production and power consumption is therefore optimal. The service life cycle of a mechanical press is considerably longer than that of a hydraulic press.

It is possible to perform the invention as a decentralised solution, meaning that compression for formation of briquettes is performed at one location and that the briquettes are stored and later transported to a facility for decomposition, as for example a biogas plant or a bioethanol plant.

By the invention it becomes possible to compress biomass to high density, to supply heat via mechanical kinetic energy, to avoid addition of water, and to use the natural water content of about 5-20% and typically 6-16% of a biomass for repeated steam explosions. The process hereby becomes rational in that it is exclusively the biomass which is treated at high temperatures—and not a large amount of water—and that this occurs in very small reaction chambers.

Compression of wood and straw is known from pressing these materials into briquettes or pellets for subsequent combustion. However, it is not known to optimise the mechanical compression for application as mechanically induced steam explosion of biomass such that cellulose and hemicellulose are made accessible for enzymatic decomposition before fermentation into ethanol or other biofuel.

By the present invention is achieved a very high specific density of the straw between 800 and 1200 kg/m$^3$, typically a bulk density between 500 and 600 kg/m$^3$, considerably reducing the size of the reaction chamber (due to high specific density) and the need for possible transport to a central processing plant (due to high bulk density). Among the special advantages achieved by the present invention is thus a compact reaction chamber. Only a few litres of reactor volume is used, i.e. less than 50 litres and typically about 10 litre, as opposed to frequently several cubic metres in other systems (5-10 m$^3$ or more).

Addition of water is avoided and the biomass, e.g. in the form of straw, is therefore treated at its natural water content of 5-20%, typical between 6 and 16%. This substantially reduces the energy requirement as the heat capacity of water is about 4.2 J/gK whereas the heat capacity of dry straw and wood is about 1.2 J/gK. A typical addition of water 10 times the weight of straw by thermochemical pre-treatment therefore increases the energy consumption with about 40 times in the direct process.

If expedient in a given process, lignin can be extracted after mechanical steam explosion, but then at temperatures below 100° C. and typically around 50-80° C. Lignin can be extracted by water only or by acids or bases according to known prescriptions for extraction of lignin. Here, typically organic acids as lactic acid, citric acid or acetic acid are applied which possibly can be added before pressing and contribute to hydrolysis as well as extraction of lignin.

The straw is impacted with greater mechanical intensity as the straw is impacted directly by the piston strokes under compression and by repeated steam explosions as well. This provides a far better accessibility for enzymes during the subsequent enzymatic reaction such as liquefaction and saccharification before ethanol fermentation and thereby a lesser need for enzyme addition.

There exist a number of commercial enzymes for liquefaction and saccharification of cellulose/hemicellulose. It is estimated that consumption can be reduced to below 50% and typically to 20% of normal consumption by conventional thermochemically processed straw.

The heat treatment of the biomass is adapted such that it runs at temperatures within a range from 40° C. to 240° C., preferably with measurable temperatures typically from 60° C. to 170° C., and particularly in the range between 60° C. and 120° C. The processing time can be adjusted between 1 and 30 min and particularly between 1 and 5 min. As only the straw is heated and processed in a compact reactor chamber there are no practical limits to the heat treatment as a function of temperature and time. The treatment can be optimised without being limited by such considerations. When needing longer time for heat treatment, including hydrolysis, the nozzle is extended into a pipe or insulated screw conveyor which allows for a retention time of 1-2 hours or more. Typically, there can be a need for supplementary heat treatment and hydrolysis for an hour at 90° C.

The straw achieves an increased water absorbing capability. It appears that straw can absorb between 2 and 15 times its own weight in water and typically between 5 and 10 times its own weight.

The straw becomes directly mixable with water and enzymes. The addition of surfactants is normally not required in order to enhance mixing with water and the action of enzymes.

A significant dissolution of lignins is achieved due to heat and presence of oxygen during the process. The partial pressure of oxygen in water is about $2\times10^{-5}$ atmospheres (1 atm=101.325 kPa); the partial pressure of oxygen in the atmosphere is about $2\times10^{-1}$; the partial pressure is thus $10^4$ times greater in the atmosphere than in oxygen-saturated water. Oxygen is therefore added by wet oxidation under pressure, i.e. 5-20 atm, typically 10 atm, but still there is limited access to the reaction of oxygen with lignin due to the addition of large amounts of water to the process. During mechanical steam explosion straw and the ambient atmosphere with about 20% oxygen are subjected to a pressure of the said max. 2000-2500 bars. The oxygen is therefore much more reactive than during conventional wet oxidation, and lignin is therefore destroyed to a greater extent.

Besides, the straw can be impregnated with gases and/or bases or acids, cf. the above mentioned thermochemical methods for pre-treatment of lignocellulose before introduction to the piston chamber. This can take place in a mixer or a free-fall mixer.

Finally, enzymes and water can be added after treatment by means of a nozzle which sprays the mixture across the dry straw in a free-fall mixer. Enzymes and water will hereby be distributed evenly across the straw, and the particular new waterabsorbing ability of the latter will in particular distribute moisture and enzymes to all parts of the straw.

The moistened straw with enzymes can now be liquefied (hydrolysed) and supplied to an enzyme-membrane reactor where cellulose and hemicellulose are finally saccharified into sugar oligo- and monomers. In the reactor, the associated membranes will retain lignin and other unconverted substances while the sugars pass on to ethanol fermentation. In other setups it may be an advantage to ferment the total mixture of lignin, sugar etc.—a so-called "whole slurry"— and to separate after fermentation and distillation. This particularly depends on the amount of lignin in the biomass.

The new technical means for use in steam explosion of biomass, preferably straw, includes a piston. This will be mounted on a crank for establishing the reciprocating movement which moves loose biomass straw from a piston chamber into a reaction chamber. The latter is preferably formed of an open pipe with a funnel-shaped nozzle in which the biomass is compressed at a pressure between 500 and 3000 bar, in particular between 1000 and 1500 bar.

Back pressure is established by means of the biomass (the straw) which is accumulated and compressed in the reaction chamber and which is moved through the compression chamber in compressed form and by the friction between the biomass and the wall of the chamber.

The length of the reaction chamber and insulation thereof are adapted according to need depending on the duration of the action of temperature. The chamber is provided with heat jacket such that the temperature can be adjusted according to need.

It is preferred that the biomass (the straw) can be cut to a few centimetres of straw length. Also, it is preferred that a cleaning of the biomass of stones and sand and other foreign bodies is performed before compression.

The press is provided with thermometers and manometers according to need.

The temperature in straw is regulated by means of the stroke force of the piston, cooling of reaction chamber and insulation of reaction chamber.

The finished, compressed straw can be crumbled afterwards, again appearing like cut straw though much softer now. The straw has, however, completely changed its character after the treatment and has become waterabsorbing, among others. The straw can absorb between 2 and 15 times its own weight, in particular 5-10 times its own weight.

Hereby it is possible to add enzymes and water simultaneously, e.g. via spray nozzles, in a free-fall mixer or other kind of mixer. Water and enzymes are thereby evenly distributed in the straw.

It is also possible to add the straw in compressed form and directly to a bioreactor, thermoreactor, chemical reactor, thermochemical reactor or other kind of reactor. Besides, it is possible to add the straw to fluid livestock manure, fluid waste water sludge etc. before a biogas process wherein the straw then will be converted in the biogas reactors into biogas with maximum yield.

A method according to the invention can be used in pre-treatment of straw for use in biogas production. A typical biogas plant degassing 100,000 tons of fluid livestock manure and delivering the gas to a decentralised combined heat and power plant may—with proper technique—without substantial further investments in the biogas plant itself utilise e.g. 10,000 tons of straw yearly as well. The biogas production will hereby be increased from about 2.5 m m$^3$ from livestock manure with about 4 m m$^3$ from the straw to 6.5 m m$^3$ in total yearly. The method provides possibility of a substantial increase in the biogas production in existing plants.

The total effect of mechanical steam explosion includes mechanical compression, heat treatment, steam explosion, oxidation and autohydrolysis.

The method according to the invention can, for example, be performed in the following way which is described on the basis of straw but which can be used analogously on other lignocellulose-containing biomasses.

Prior to mechanical steam explosion, the process starts by feeding dry cut straw, dry sawdust or similar lignocellulose into a piston chamber. A piston on a crank moves loose straw into a tubular reaction chamber. The piston moves back and forth by the crank and moves new straw into the reaction chamber by each stroke. Compressed straw is pushed through the pipe by renewed feeding of straw and compression thereof.

The straw can be impregnated by gases, acids or bases according to need before being introduced to the piston chamber. The autohydrolysis can be enhanced hereby and pH be lowered further in the treated material, i.e. to pH 1-4, typically pH 2. Alternatively, base can be added and thus a basic hydrolysis is performed in addition to the mechanically induced effects.

The compressed straw can be crumbled subsequently and is thus open to addition of water and enzymes in a free-fall mixer or other kind of mixer.

The treated straw is supplied to a biogas process, a bioethanol process or other fermentation process or process for producing biofuel, organic acids or other organic biological products like paper, industrial chemicals, fodder, or other material.

Commercially available mechanical components can be utilised for the invention, including lines for handling straw in the form of big bales, including conveyor belts, tearing up, comminution to a desired particle size by means of hammer mills, separation of stones, sand and other contaminants before mechanical steam explosion.

Commercial briquette presses can thus be used as well after modification as to provide the process parameters which are necessary for inducing steam explosion in straw and similar biomass.

After the mechanical steam explosion, the material can fit into production of bioethanol, biogas or other form of biofuel; typically it will be bioethanol. In the production of bioethanol there are in principle two systems which either use the material directly in the ethanol process or which uses an extraction of lignin before the ethanol process.

Finally, the fact that the treatment results in compression of the material to high density can be utilised in several ways. Firstly, a subsequent treatment in thermochemical or other reactor can occur at high density as the straw is compressed and anyway can be introduced in reactor (as e.g. a bioreactor). However, it can be utilised as well that the biomass, e.g. straw, can be collected locally and treated in local, decentralised processing stations where it is stored in compressed condition before being transported to a central processing plant, e.g. a bioethanol plant.

The local treatment thus includes collecting e.g. straw in amounts of 10,000-50,000 tons or the like, treating in a straw handling line, pressing etc. as described by the invention, and weighing-in, registration and quality control before storing locally.

It is noted that treatment and compression are here utilised to a total logistic solution for collecting in the magnitude 0.5-1 m tons of straw or more to a central bioethanol plant.

Furthermore, acid, base or gases are added as catalysts in the treatment and at the same time as antimicrobial agents during storage. Hereby is avoided that the biomass is attacked by microorganisms during storage—the biomass is quite simply preserved. At the same time it is cleaned, registered and quality controlled via the total pre-treatment and stored as such in relation to type and quality.

According to a special embodiment, the method according to the invention is peculiar in that after leaving the reaction chamber, the biomass is moved directly to a reactor selected among an enzyme reactor, a thermal chemical reactor, a thermal reactor, a chemical reactor, a biological reactor, or a different reactor.

According to a special embodiment, the method according to the invention is peculiar in that after leaving the reaction chamber, the biomass is stored locally and that subsequent processing is performed in a central plant.

According to a further special embodiment there is indicated a method for making fodder, as for example cattle fodder. This is effected by ensilation of straw which is treated by the mechanically induced steam explosion. This enables ensiling the straw, either independently or by an admixing of hay, maize or other crop for ensilation. This improves the feed value of straw and mixed ensilations, including increasing the dry matter content, protein content and general digestibility of the ensilage.

According to a further special embodiment there is indicated a method for treating biomass in the form of wood chips to paper pulp or other fibre product where the mechanically induced steam explosion constitutes an interjected pre-treatment. This pre-treatment occurs before a conventional thermochemical treatment (KRAFT) in sodium hydroxide (NaOH) and sodium sulphide ($Na_2S$).

This entails that the conventional treatment can be effected with less consumption of water, chemicals and energy in a smaller volume, and which therefore is performed in a more cost-effective way.

DESCRIPTION OF THE DRAWING

In the following, the invention will be explained in more detail with reference to the enclosed drawing wherein.

DETAILED DESCRIPTION OF EMBODIMENTS OF THE INVENTION

FIG. 1:

Illustrates the technical arrangement and the operation of mechanical steam explosion of straw before a biogas process.

Figure 1:
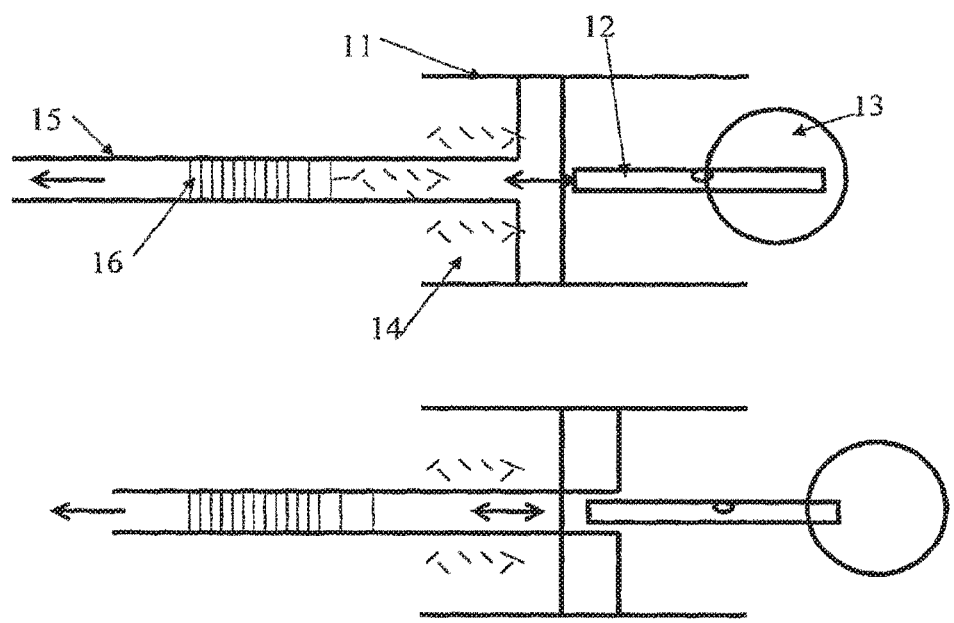
FIG. 1 shows schematically the design of a piston press for use in establishing mechanical steam explosion in a biomass.

In FIG. 1 are used the following reference numbers: 11 is a piston chamber; 12 is a piston; 13 is a crank; 14 is loose straw; 15 is a reaction chamber (pipe) and 16 is compressed straw.

FIG. 2:

Illustrates a flow diagram for utilising the invention for producing bioethanol from straw. The straw 1) is received, torn up and cleaned in a straw handling line before treatment in 2) press and possible supplementary hydrolysis before 3) tearing up compressed straw into loose straw. This loose straw can now be sprayed with or added a suitable mixture of water and enzymes for performing 4) mixing and liquefaction, also called dedicated hydrolysis. Hydrolytic enzymes are added to water, and this enzyme-water mixture is added to straw such that the dry matter content is optimal with regard to hydrolysis as well as the remaining processes in the total bioethanol production. It is noted that the invention enables adjusting the dry-matter/water/enzyme ratio optimally as the straw is pre-treated in dry condition and is not to be dewatered before hydrolysis, e.g. because the straw has not been pre-treated by conventional steam-explosion in large amounts of water. The liquefaction or dedicated hydrolysis is effected optimally in the temperature range 40-80° C., typically 50-55° C. and at pH 4-7, typically pH 5.0-5.5. The duration of the dedicated hydrolysis is 1-100 hours, typically 24-72 hours, particularly 48 hours. This dedicated hydrolysis can be further extended via a membrane enzyme reactor where the hydrolysis is extended until the complete decomposition of sugar polymers into sugar oligomers and monomers. Temperatures and pH which are optimal to the hydrolysis in a membrane reactor are maintained, and an associated membrane only allows dissolved sugar oligomers and monomers to pass through the membrane, whereas lignin, unconverted straw and enzymes are retained in enzyme reactor. The enzyme-membrane system typically consists of a screening via a vibrating screen, drum screen or micro-screen for retaining larger particles in enzyme reactor, typically particles between 10 and 200 µm (micrometers), preferably 50-150 µm and typically under 100 µm. This screened material is now filtered across a membrane, typically an ultrafiltration membrane (UF-membrane) with a pore size of 10-100 nm (nanometres), preferably 25-75 nm and typically around 50 nm. Such membranes have a molecular weight cut-off (MWCO) of 5-15,000 Dalton and typically around 10,000 Dalton. This membrane allows sugar to pass whereas lignin is retained, constituting a lignin concentrate. In a preferred configuration, UF-filtration is combined with a RO-filtration whereby the dissolved sugars are concentrated before fermentation, and where the permeate, the pure water, is recycled to enzyme reactor or before it. The concentrated sugar is supplied to 6) bioreactor for fermentation into bioethanol, subsequent distillation etc. The process around 5) enzyme-membrane reactor can consist of screening or UF-membrane only or in combination as well as the membrane system can include RO-filtration. The most important advantage associated with the system is that the dissolved sugars—meaning the product of the enzyme activity—are continuously removed whereby product inhibition of the enzymes is eliminated. Furthermore, the stay time of biomass particles in the enzyme-membrane reactor is disconnected from the hydraulic stay time, also contributing to a complete hydrolysis of the biomass. Finally, the sugars are concentrated in RO-plant for optimal concentration of 10-30%, typically around 20%, ensuring an optimal ethanol concentration during fermentation and distillation.

FIG. 3:

Illustrates a flow diagram for injection of straw into a biogas reactor wherein the straw is torn up and cleaned in a straw handling line before actual pre-treatment in the press. The pre-treated and compressed straw can now be supplied, directly or indirectly, to a biogas reactor, or for that matter to a different reactor. Here it is utilised that the straw is pre-treated and therefore viscous and easily dissolved in the reactor liquid as well as compressed to high specific density of 0.5-1.5, preferably 0.8-1.2 and typically around 1. It is essential that the compressed straw has high density as the straw therefore can sink into the liquid where it is suspended within a short period of time and distributed within the entire reactor liquid volume. No float layer or other preventing conversion into biogas is thus formed. It is also essential that the straw has changed its character and has become very viscous—i.e. waterabsorbing—as this property allows the straw to be suspended and distributed in the entire reactor liquid volume. The direct addition can be effected by connecting the discharge pipe, or extension nozzle, on the press directly to bioreactor while being aware that compressed straw run in the extension pipe here encounters a liquid with an overpressure which is proportional to the liquid level in the reactor, e.g. 1 bar or more. However, the compressed straw in the extension pipe is so compressed and is advanced at so great overpressure (up to the mentioned 2000 bars) that the straw, without risking run-back of liquid or leakage of biogas, can be introduced at the bottom of reactor and therefore under the liquid surface. It is also possible to supply the straw via another screw system where a long inclining or vertical screw conveyor moves the straw up to a short inclining feed screw which opens under the liquid surface. Hereby is also avoided run-back of liquid and escape of biogas. The straw will also here sink down into the reactor liquid and be suspended within a short time. By short time is meant between 1 and 120 min, preferably 30-90 min and typically in less than 1 hour. This is a short period of time in the light of a typical hydraulic stay time in a biogas reactor of 10-90 days. The straw can also be supplied indirectly to bioreactor via admixing into another biomass, typically fluid livestock manure, sludge, waste water and the like which is supplied to biogas reactor via pumping. Often a receiving reservoir or receiving tank is provided for liquid biomass in a biogas plant, and the straw can here be added from the press, suspended and pumped into bioreactor with the other biomass. If pre-treatment, compression, storage etc. are performed in decentralised collecting stations before transport to the bioenergy plant, the straw will typically be introduced via another screw conveyor or other lock-feeder system.

Figure 2:
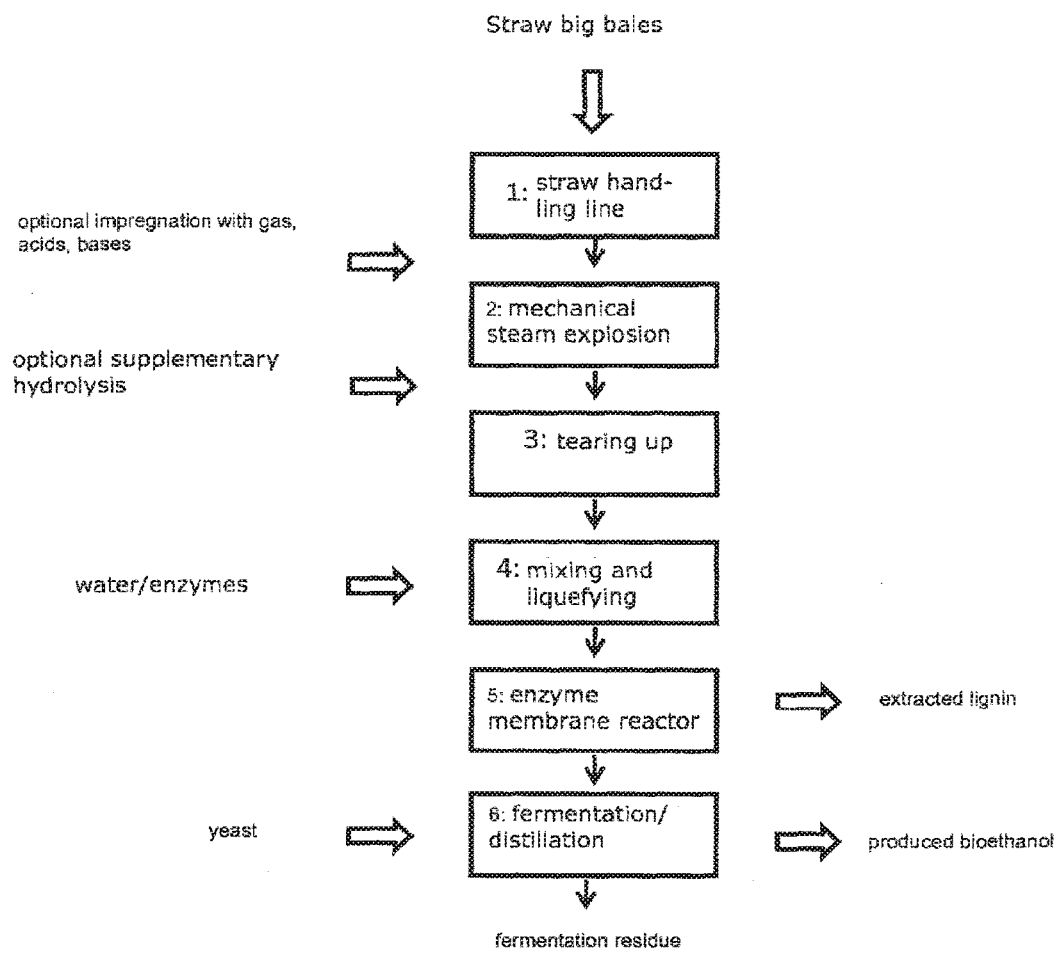
FIG. 2 shows a diagram for illustrating various embodiments of a method according to the invention.
Figure 3:
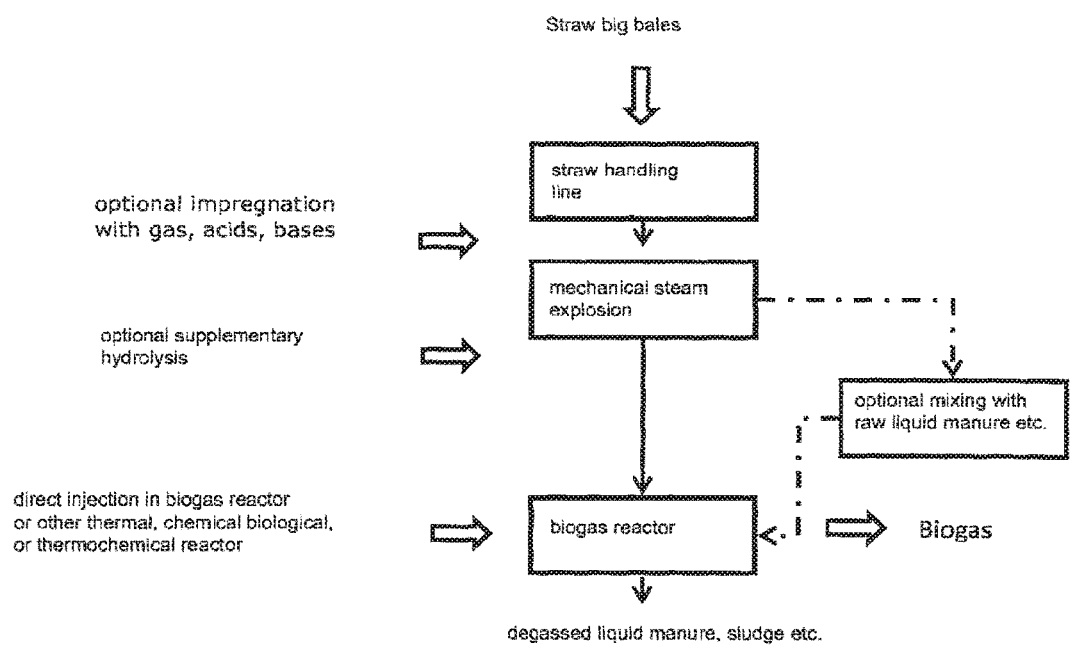
FIG. 3 shows a diagram for illustrating a principle in utilising mechanical steam explosion as a technique for simultaneous pre-treatment and feeding of straw into a biogas reactor, alternatively direct or indirect feeding into thermal, chemical, thermochemical or other bioreactor.
Figure 4:
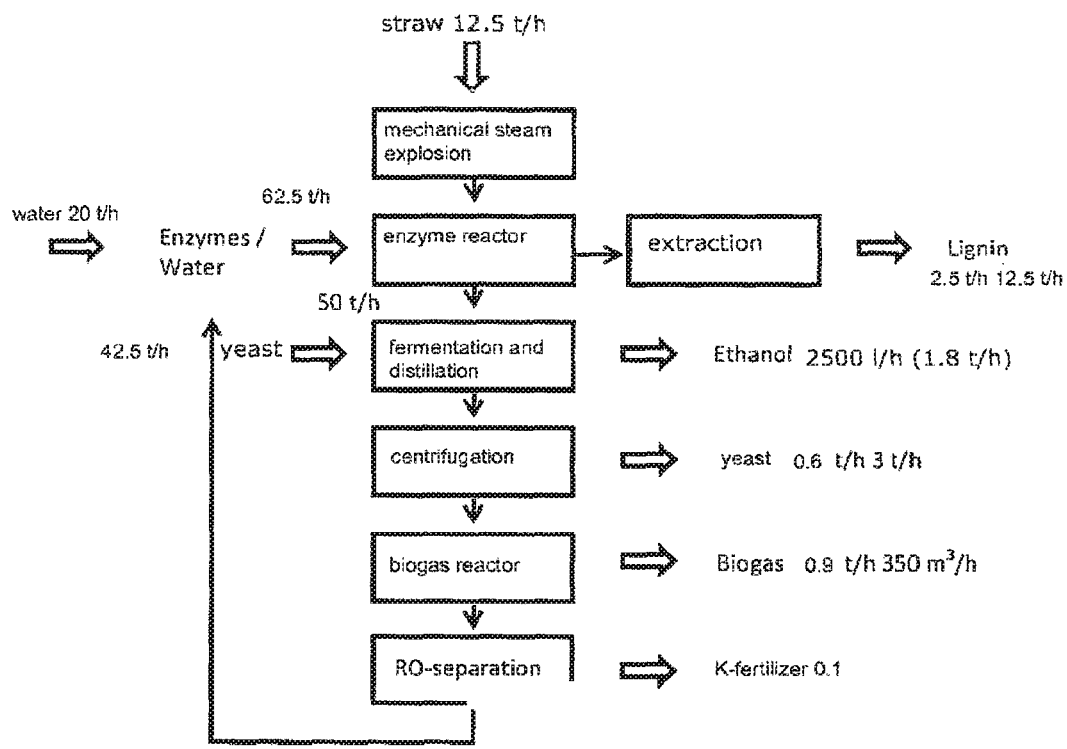
FIG. 4 shows a diagram for illustrating a principle in utilising mechanical steam explosion as a pre-treatment of straw before a bioethanol process and the main principles in the bioethanol process, and wherein lignin is extracted in an enzyme reactor.
Figure 5:
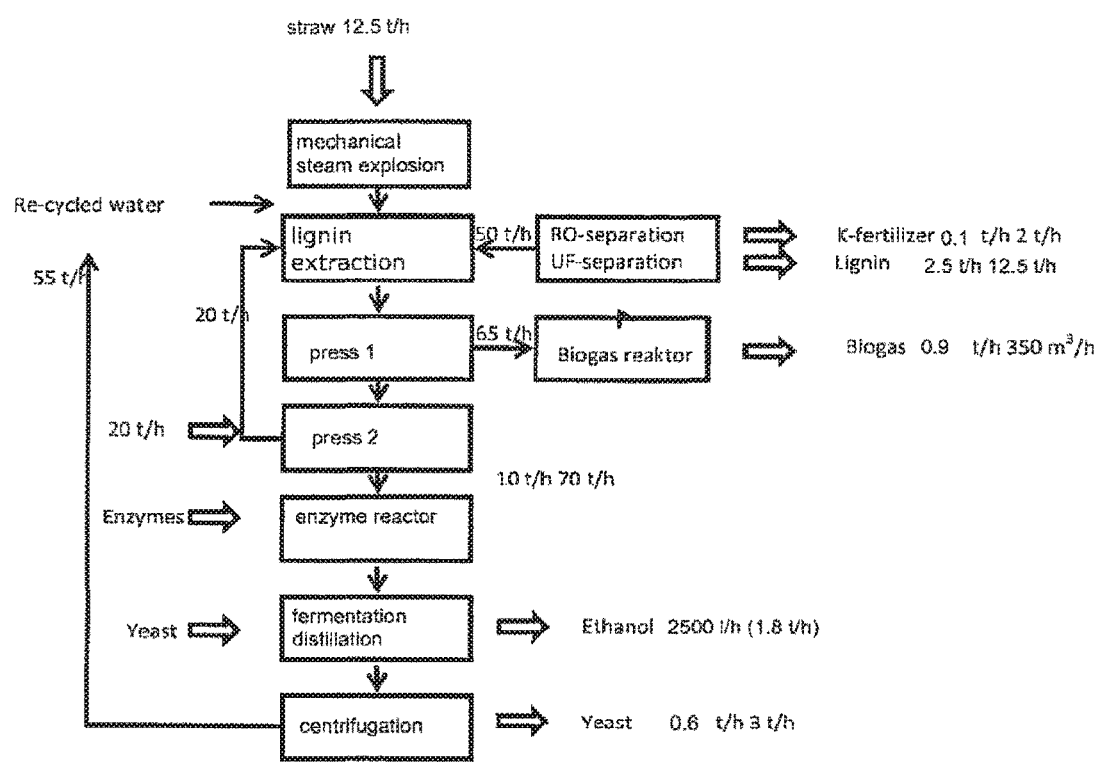
FIG. 5 shows a diagram for illustrating a principle in utilising mechanical steam explosion as a pre-treatment of straw before a bioethanol process and the main principles in the bioethanol process, and wherein lignin is removed by a pressing action.
Figure 6:
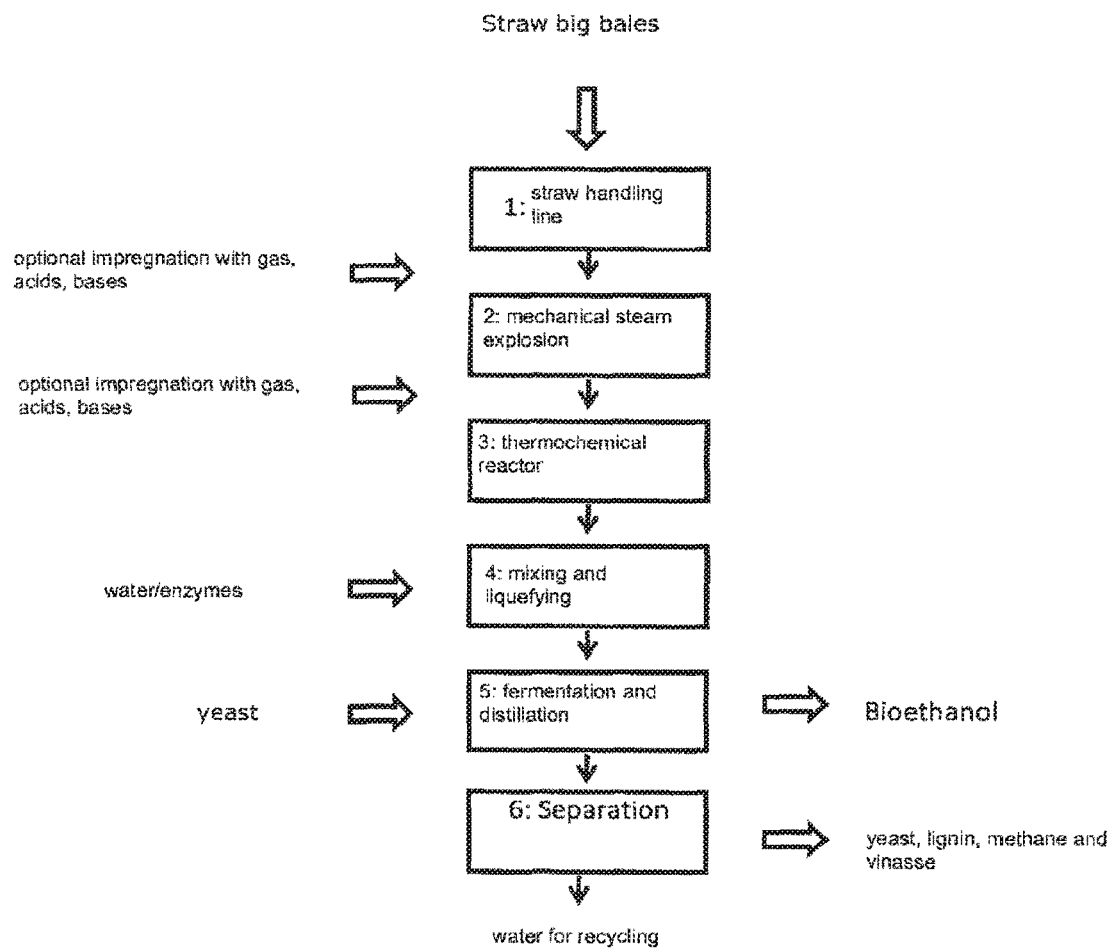
FIG. 6 shows a diagram for illustrating a principle in integration of mechanically induced steam explosion in a bioethanol process containing a typical thermochemical or other reactor for pre-treatment.
Figure 7:
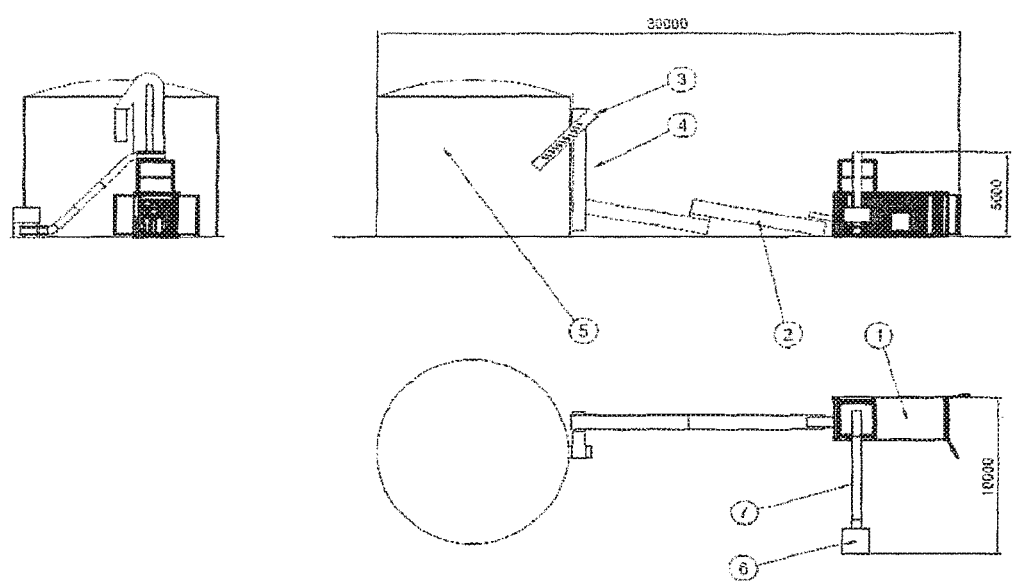
FIG. 7 shows schematically a biogas plant in which is used a piston press for establishing mechanical steam explosion in a biomass as pre-treatment of the biomass before introducing into a bioreactor.
Figure 8:
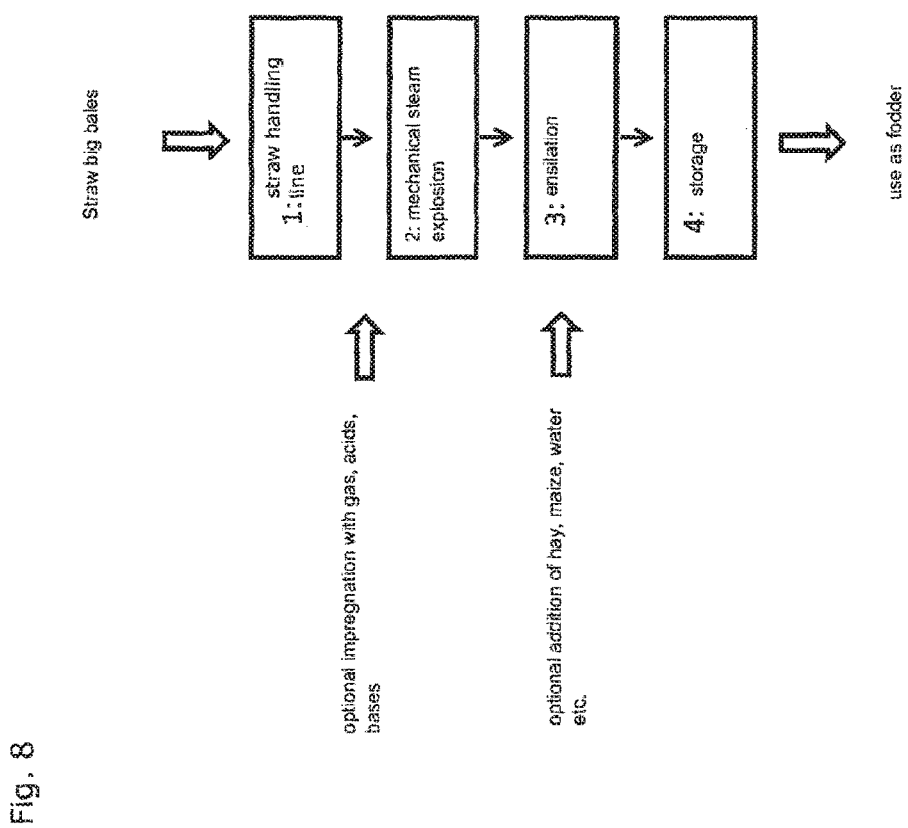
FIG. 8 shows a diagram for illustrating a principle in integration of mechanically induced steam explosion in a method for producing fodder, as for example cattle fodder.
Figure 9:
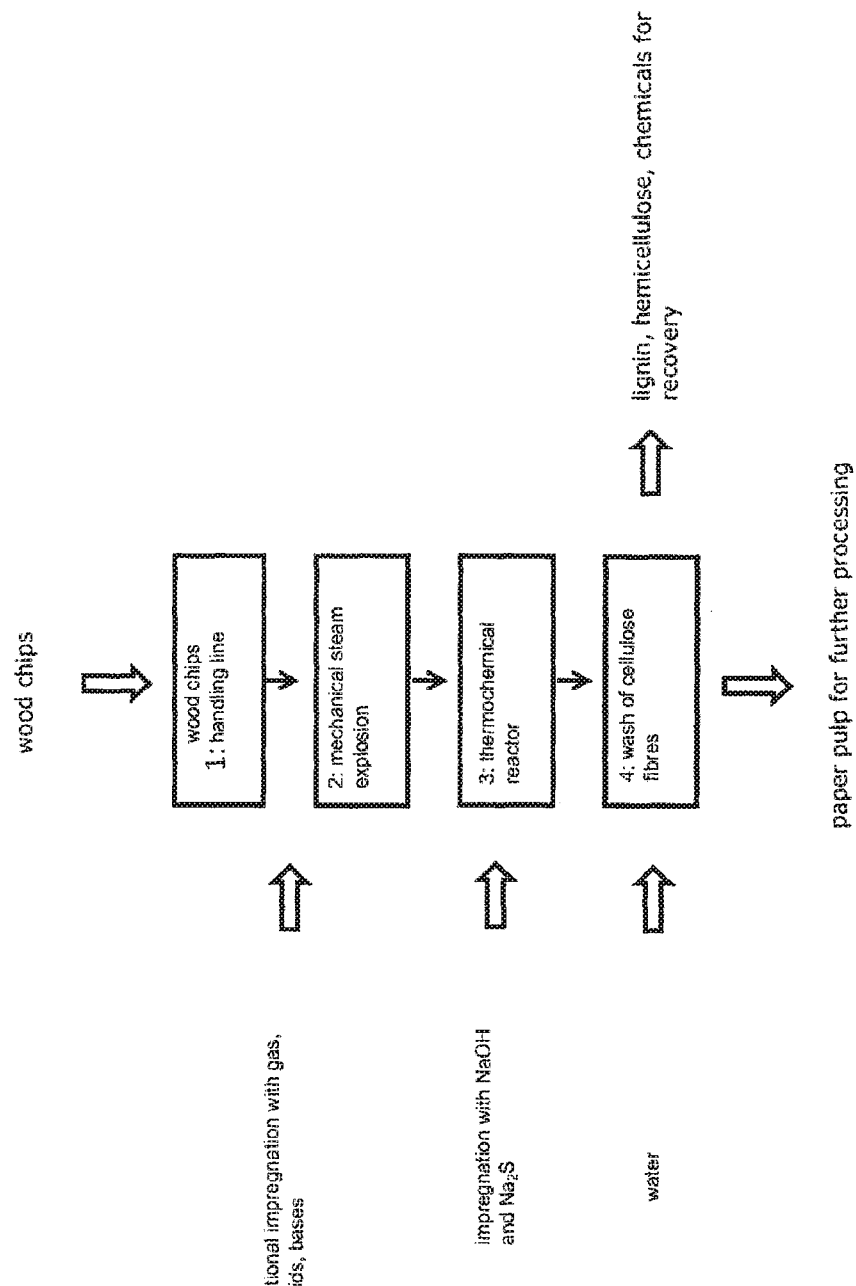
FIG. 9 shows a diagram for illustrating a principle in integration of mechanically induced steam explosion in a method for treating biomass in the form of wood chips into paper pulp or other fibre product before a conventional thermochemical treatment.

FIG. 4:

Illustrates a flow diagram for a bioethanol process configuration wherein lignin is removed after pre-treatment and before fermentation, cf. also FIG. 2 (see this). The fermentation and distillation are optimal, cf. description to FIG. 2, and as the fermentation occurs without substantial amounts of lignin, the fermentation will result in a pure yeast that can be separated from the distillate by centrifugation. The concentrate from the centrifuge constitutes a yeast fraction whereas the rejected water constitutes a thin liquid fraction with remains of dissolved sugar, yeast cells, lignin etc. which advantageously can be degassed in biogas reactor for production of biogas and for conditioning the liquid before RO-filtration and making of vinasse (K-fertiliser) for fertilising purposes and pure water for recycling. Examples of realistic key figures for production flows are indicated in the Figure. Input is 100,000 tons of straw yearly or 12.5 t/h at 8000 operational hours. The straw is assumed consisting of 40% cellulose, 30% hemicellulose, 20% lignin and 10% water.

FIG. 5:

Illustrates a flow diagram for a situation in which the biomass contains larger amounts of lignin and where thus a specific lignin extraction is inserted after pre-treatment and before fermentation etc. This lignin extraction has the particular advantage that the pre-treated straw, cf. the invention, is dry and hydroscopic and can therefore be added a liquid which is optimised with regard to the extraction of lignin. In a preferred configuration, organic acids like citric acid, lactic acid, acetic acid and similar organic acids are used for extracting lignin at 40-120° C., preferably 60-100° C. and typically 80° C. at final pH of 1-6, preferably 2-4 and typically pH 3. It is noted that these acids can be added before the press, cf. the invention, and if so, only water is added after the press for lignin extraction. Hereby lignin and partly hemicellulose and potash salts are extracted whereas pure cellulose fibres are left to further processing. The extraction occurs by adding a mixture of water and organic acid to the treated straw after which the liquid after some time undergoes mechanical pressing in one or two steps. The cellulose fibres continue in the process whereas the lignin-acid mixture is supplied to a biogas process where particularly hemicellulose and dissolved sugars and the organic acids are converted into biogas while lignin passes biogas reactor for subsequent concentration via UF-membrane. After UF-membrane, K-salts are concentrated in RO-membrane whereas the permeate, the pure water, is recycled for renewed extraction. The pure cellulose fibres are supplied to enzyme membrane reactor, cf. FIG. 2, before fermentation and distillation, and finally centrifugation for making a pure yeast fraction. In the Figure are mentioned examples of realistic production figures and material flows. Input is 100,000 tons of straw yearly or 12.5 t/h at 8000 operational hours. The straw is assumed consisting of 40% cellulose, 30% hemicellulose, 20% lignin and 10% water.

FIG. 6:

Illustrates in more detail a so-called "whole slurry" process configuration where no separation of lignin occurs after pre-treatment but where the entire pre-treated biomass is supplied to fermentation and distillation, and only after distillation it is separated into the main components yeast cells, methane via a biogas process, lignin and vinasse, where vinasse consists of nutrient salts, in particular potash, phosphorus and nitrogen. The configuration is initiated by collecting and a first treatment of straw via 1) a straw handling line where the straw is torn up to lengths of 1-20 cm, typically 5-10 cm, and is cleaned from contaminants via air-assisted cyclone before a hammer mill which further reduces the straw length to 0.1-5 cm, typically 1-2 cm, before 2) treatment in mechanical press, cf. the invention. In that connection it is possible and probable that the straw is collected, pre-treated, quality controlled, registered, weighed-in and stored locally in decentralised collecting stations before transport to a central biogas plant. In the central bioenergy plant, the compressed straw—in compressed form—is supplied to a 3) thermochemical reactor where the straw is added water according to need and subjected to a supplementary hydrolysis via direct injection of steam such that the straw is exposed to temperatures between 60 and 220° C., typically 120-180° C. and particularly 140-60° C., and incubated for a suitable time, i.e. 1-120 min, typically 10-60 min and particularly 30-40 min. The straw is now ready for 4) enzymatic liquefaction, also called dedicated hydrolysis, and suitable enzymes are added to water, and this enzyme-water mixture is added to the straw such that the dry matter content is optimal in relation to hydrolysis as well as the remaining processes in the total bioethanol production. It is noted that the invention enables adjusting the dry matter/water/enzyme ratio optimally as the straw is pre-treated in dry condition and is not to be dewatered before hydrolysis. Correspondingly, it is possible to perform a supplementary pre-treatment in the thermochemical reactor with an optimal ratio between water/dry matter and possible catalysts. The liquefaction or dedicated hydrolysis is effected optimally in the temperature range 40-80° C., typically 50-55° C. and at pH 4-7, typically pH 5.0-5.5. The duration of the dedicated hydrolysis is 1-100 hours, typically 24-72 hours, particularly 48 hours. Fermentation and distillation 5 occurs substantially as SSF fermentation (Simultaneous Saccharification and Fermentation), i.e. simultaneous saccharification and fermentation, and the distillation as vacuum steam distillation, cf. the known principles thereof. A special feature is, however, that the fermentation is extended to 2-14 days, typically 8-12 days and particularly 10 days against normally 1-3 days for conventionally operated plants. This is to achieve maximum specific ethanol production while simultaneously considering the lignin content in the whole slurry system. Fermentation occurs at standard pH and temperatures as well as distillation occurs at standard conditions therefor. During the separation, 6) separation of yeast cells from the distillate forms part thereof via a new technique adapted to this type of distillate containing yeast cells. The distillate is subjected to a "dissolved air flotation", i.e. injected and dissolved air bubbles which lift up the yeast to the liquid surface where it is conducted away from the liquid and centrifuged. Hereby is achieved a pure yeast substrate which can be used a protein fodder. The residual liquid with a content of dissolved lignin, residual amounts of sugar, yeast cells and substrate are supplied to a biofilm reactor for production of biogas. Lignin generally passes through the biogas reactor whereas residual sugar etc. is converted to biogas. After biological degassing, the liquid thus contains a pure lignin fraction and is well suited for settling and ultrafiltration for separation of lignin. A pure lignin fraction is hereby produced. At the same time, the UF-filtration enables separation of dissolved nutrient salts from the residual liquid via a final RO-separation (RO: Reverse Osmosis) and evaporation. The concentrate from the RO-separation constitutes vinasse while the permeate is pure water which is recycled to steps 3 and 4. Hereby, the production process is complete and thus is produced bioethanol, yeast substrate, methane, lignin and vinasse from the straw.

FIG. 7:

Illustrates a plant including a container 1 that contains a dispensing silo and a press of the type shown in FIG. 1, two heat treatment screws 2, a feeding unit 3, a first conveyor 4, a bioreactor 5, a filling unit 6 an a second conveyor 7.

The shown plant operates in that biomass in the form of cut straw, maximum length 40 mm, is filled into the filling unit 6.

The straw is moved on by the second conveyor 7 to the dispensing silo, which is an integrated part of the container 1, and down into the press in which a briquetting process is performed. After the briquetting process, the briquettes are moved via a discharge pipe (also called an extension nozzle) on the reaction chamber of the press to the heat treatment screws 2. The heat treatment screws 2 can be adjusted in temperature and time for passage. The heat treatment screws have a capacity of 750-1200 kg which typically corresponds to one hour of production.

Conveyor 4 moves the briquettes to the feeding unit 3. The feeding unit 3 is adapted to introduce the briquette under liquid level in the bioreactor in such a way that gas leakage from the bioreactor 5 will not occur during the feeding of the briquettes.

Alternatively, the briquettes can be moved by the heat treatment screws 2 directly from the piston press into the bottom of the bioreactor 5 below liquid level.

FIG. 8:

Illustrates a method for producing fodder, as for example cattle fodder, via ensilation of treated straw. The mechanically induced steam explosion enables ensiling the straw, either independently or via admixing cut grass, maize or other crop for ensilation. This improves the feed value of straw and mixed ensilations by i.a. increasing the dry matter content, protein content and general digestibility of the ensilage.

FIG. 9:

Illustrates a method for processing biomass in the form of wood chips into paper pulp or other fibre product where the mechanically induced steam explosion constitutes an interjected pre-treatment before the conventional thermal chemical processing (KRAFT) in sodium hydroxide (NaOH) and sodium sulphide ($Na_2S$). This entails that the conventional treatment can be effected with less consumption of water, chemicals and energy in a lesser volume, and which therefore overall is performed in a more cost-effective way.

The invention claimed is:

1. A method for processing a biomass containing lignocellulose, wherein the cellulose and hemicellulose are made accessible for further processing comprising the following steps:
   a) collecting and treating the biomass in local, decentralized pre-processing stations where it is stored in compressed condition; then
   b) subsequent processing in a central processing plant selected from a bioethanol plant and/or a biogas production plant
   wherein the treating at the pre-processing stations comprises repeated compressions of the biomass in a reciprocating piston press, where loose biomass is continuously fed into a piston chamber in front of a piston which moves the loose biomass into a tubular reaction chamber with sufficient force to compress the biomass to a pressure to mechanically induce water vapor explosion and autohydrolysis while simultaneously moving the compressed biomass through the reaction chamber.

2. The method according to claim 1, further comprising cleaning of the biomass of stones and sand and other foreign bodies is performed prior to the decentral preprocessing step, in particular before the repeated compressions.

3. The method according to claim 1, further comprising a step where the biomass, after leaving the reaction chamber, is moved to the central processing plant, which comprises a reactor selected from the group consisting of an enzyme reactor, a thermochemical reactor, a thermal reactor, a chemical reactor, a biological reactor, and a different reactor.

4. The method according to claim 1, further comprising a step at the central processing plant, the wherein the compressed biomass is subsequently torn up and enzymes and water are mixed together and sprayed over the torn up biomass.

5. The method according to claim 3, the central processing includes a thermochemical reactor where water is added to the biomass and subjected to a supplementary hydrolysis under elevated temperatures between 60-220° C. via direct injection of steam.

6. The method according to claim 1, wherein the processing of the biomass at the central processing plant comprises forming the biomass into a slurry with water which is then supplied to fermentation and distillation without the separation of lignin from the slurry.

7. The method according to claim 1, comprising a step where the biomass is moved to an enzyme reactor and a subsequent fermentation step at the central processing plant.

8. The method according to claim 1, comprising a step where the biomass is added to fluid livestock manure or fluid waste water sludge etc. before subsequent processing at the biogas production plant to produce biogas.

9. The method according to claim 8, comprising a step where the biomass is added at a level below a surface in a reactor tank of the biogas production plant.

10. The method according to claim 1, wherein the biomass is straw.

* * * * *